United States Patent [19]

Doty

[11] Patent Number: 4,936,306
[45] Date of Patent: Jun. 26, 1990

[54] DEVICE AND METHOD FOR MONITORING EVOKED POTENTIALS AND ELECTROENCEPHALOGRAMS

[76] Inventor: James R. Doty, 614 Concerto La., Silver Spring, Md. 20901

[21] Appl. No.: 802,371

[22] Filed: Nov. 27, 1985

Related U.S. Application Data

[63] Continuation-in-part of Ser. No. 702,251, Feb. 15, 1985, abandoned.

[51] Int. Cl.$^5$ .............................................. A61B 5/04
[52] U.S. Cl. ..................................... 128/642; 128/731
[58] Field of Search ............................... 128/639–643, 128/131–732, 784–785, 790–791, 644

[56] References Cited

U.S. PATENT DOCUMENTS

| Re. 28,990 | 10/1976 | Hon et al. | 128/642 |
|---|---|---|---|
| 3,737,579 | 6/1973 | Bolduc | 128/785 |
| 3,750,650 | 8/1973 | Ruttgers | 128/642 |
| 3,807,387 | 4/1974 | MacNichol, Jr. | 128/731 |
| 3,826,244 | 7/1974 | Salcman et al. | 128/642 |
| 3,964,470 | 6/1976 | Trombley | 128/642 |
| 4,010,758 | 3/1977 | Rockland et al. | 128/785 |
| 4,080,961 | 3/1978 | Eaton | 128/642 |
| 4,090,752 | 5/1978 | Long | 128/641 X |
| 4,149,528 | 4/1979 | Murphy | 128/642 |
| 4,157,710 | 6/1979 | Abitbol | 128/642 |
| 4,217,913 | 8/1980 | Dutcher | 128/785 |
| 4,281,659 | 8/1981 | Farrar et al. | 128/642 X |
| 4,299,232 | 11/1981 | Zilianti | 128/643 X |
| 4,301,806 | 11/1981 | Helfer | 128/642 |
| 4,320,764 | 3/1982 | Hon | 128/635 |
| 4,321,931 | 3/1982 | Hon | 128/642 |
| 4,355,642 | 10/1982 | Alferness | 128/642 |
| 4,501,276 | 2/1985 | Lombardi | 128/642 |
| 4,658,825 | 4/1987 | Hochberg et al. | 128/642 X |
| 4,658,835 | 4/1987 | Pohndorf | 128/785 |
| 4,685,466 | 8/1987 | Rau | 123/642 X |

FOREIGN PATENT DOCUMENTS

| 2749048 | 5/1979 | Fed. Rep. of Germany | 128/642 |
|---|---|---|---|
| 2830412 | 1/1980 | Fed. Rep. of Germany | 128/643 |
| 4327686 | 11/1968 | Japan | 128/642 |

Primary Examiner—Angela D. Sykes
Attorney, Agent, or Firm—Banner, Birch, McKie & Beckett

[57] ABSTRACT

Device and method for monitoring evoked potentials and/or electroencephalograms including a novel unipolar spiral coil electrode. The unipolar electrode includes a user holder member formed of non-conductive material and having an outside surface adapted to be grasped by the physician's fingers. A spiral coil formed of a conductive material and having a pointed or beveled tip extends forward from the user holder member. The coil is directly attached to the user holder member such that when the user holder member is grasped by the physician's fingers, pressed against the patient's skin and rotated, the tip pierces the patient's skin and the spiral coil is twisted through the epidermis to a distance sufficient to secure the user holder member to the patient but not great enough to pierce the underlying bone. To assist in manipulating the user holder member, the user holder member on its outer surface includes a friction increasing device such as a pair of projecting ears, a knurled surface, or a knob. An electrically conducting wire connects to the holder member, and thus the spiral coil, either through a permanent or a removable connection, and exits preferably rearwardly from the holder member. The wire has an opposite connector end adapted to be connected to a device for monitoring the electrical activity of the brain.

46 Claims, 4 Drawing Sheets

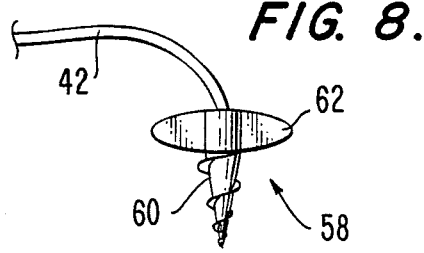
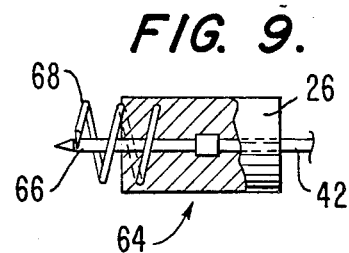
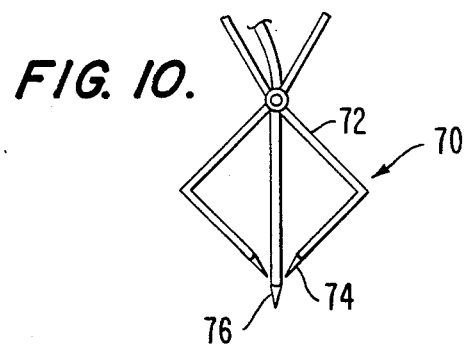
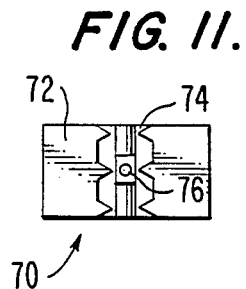
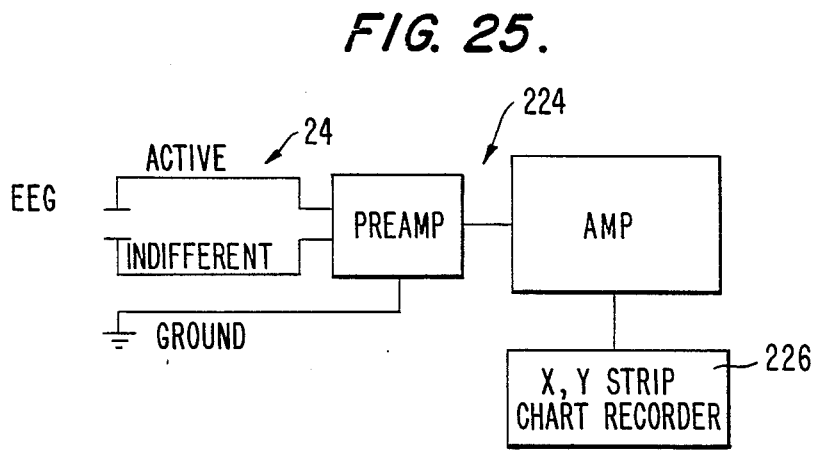
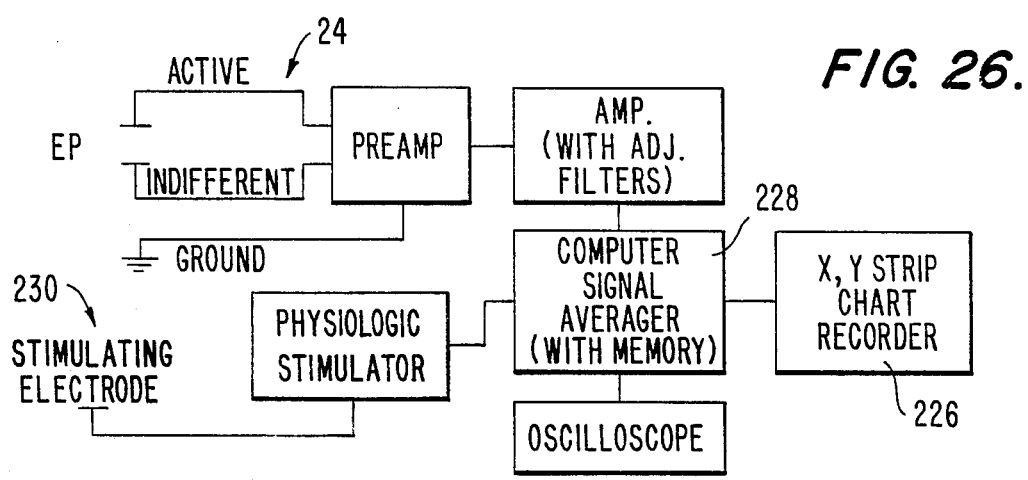

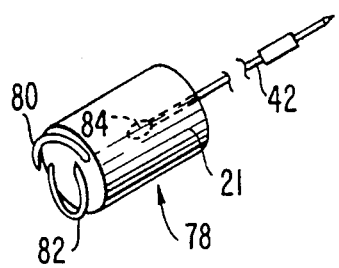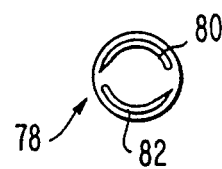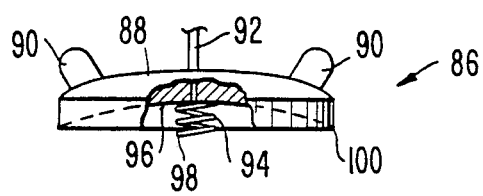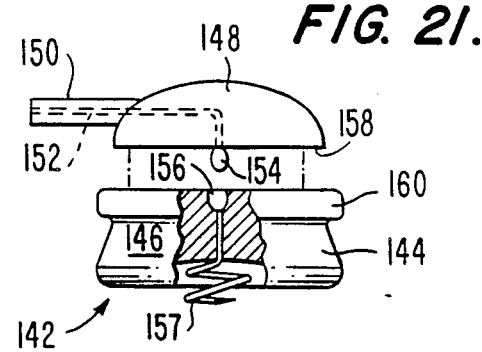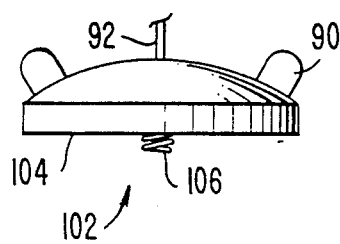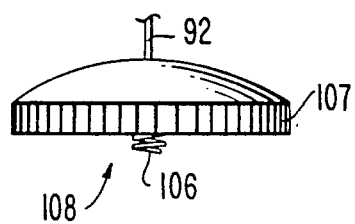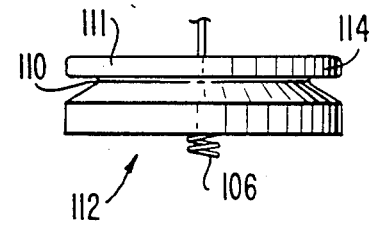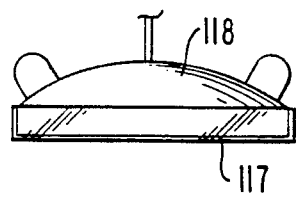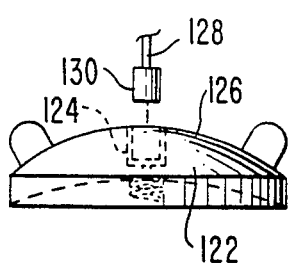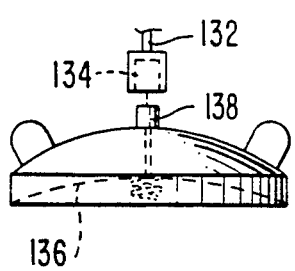

DEVICE AND METHOD FOR MONITORING EVOKED POTENTIALS AND ELECTROENCEPHALOGRAMS

BACKGROUND OF THE INVENTION

The present application is a continuation-in-part of U.S. Application Ser. No. 702,251, filed Feb. 15, 1985, now abandoned.

The present invention relates to devices and methods for monitoring evoked potentials (EPs) and electroencephalograms (EEGs) in the operating room, in the intensive care unit, and in the laboratory. It more particularly relates to unipolar electrodes adapted to be secured to the patient's or laboratory animal's scalp or skin over his adjacent spinal cord for monitoring electrical activity of his nervous system including his brain and spinal cord.

The intraoperative monitoring of EPs and EEGs in humans promises a means of reducing the incidence of neurologic injury during selected neurosurgical, orthopedic, and vascular operations. This monitoring can result in the reduction of damage done to individuals during anesthesia and during operations. However, it is only recently that the intra-operative monitoring of evoked potentials has become technically feasible and many surgical procedures are now being monitored with evoked potentials.

The electrical potentials emanating from the nervous system are quite small in amplitude and great care must be taken to record them accurately in the operating room where great electrical and mechanical noises are present. Conventional contact electrodes have been used in the past for monitoring EPs and EEGs. Each of the various electrodes known in the past though has its individual shortcomings, and no satisfactory electrode until now has been developed for effectively monitoring EPs and EEGs.

The most commonly used intraoperative electrode is the cup/disc electrode, which is applied to the scalp using collodion or other adhesive substance after the scalp has been abraded. An electrically conductive paste is then inserted into the top of the cup/disc and adhesive tape is used to anchor the electrode to the scalp at the desired location. Loss of adhesion frequently results though due to the patient's sweating or due to surgical manipulation. This changes the resulting wave-form configuration and can make interpretation thereof difficult, if not impossible. Difficulties have also been experienced with this electrode in obtaining consistently low impedances oftentimes requiring repeated abrading of the scalp and the repeated applications of conductive pastes. Although the electrode itself can be sterilized, the conductive paste and adhesive tape cannot be sterilized, thus making it impossible to place these electrodes in a sterile field.

The needle electrode of the prior art is simply a straight wire usually of platinum, silver or stainless steel having a sharp tip. Pressure is exerted on the needle to apply it, causing the tip thereof to penetrate the scalp epidermis. The needle is then taped into place. It has been found that the impedances with the needle electrode are generally smaller than with the cup/disc electrode. Since the only adherence to the scalp is with adhesive tape, with only minimal movement of the electrode or of the patient, the electrical signal is altered or the electrode is caused to fall completely out. If it falls out, there is difficulty in placing it in the same exact location repeatedly, since after piercing the skin, one is unable to know exactly where the electrode is located beneath the skin.

The flat plate electrode of the prior art is used on the scalp and also is used typically over the peripheral nerves. It comprises a usually circular metal plate which, after the placement of conductive gels/paste, is applied to the skin and then suitable tape is applied holding it in place. The primary disadvantage of this type of electrode is its easy loss of adhesion and the difficulty in using it for extended periods of time due to the loss of conductance across the scalp-electrode interface.

A stainless steel wire electrode is known and it is attached to the scalp by first placing the wire subcutaneously with a needle and then out of the skin, similar to a typical surgeon's stitch. The ends are braided after the needle has been removed and the braided ends are then attached to an appropriate monitoring device. It is important to note that this type of electrode is typically used only on animals and never on humans. The disadvantages of this electrode include the difficulty in obtaining low impedances and the electrical interferences caused when the loop, even though firmly attached to the scalp, moves relative to the scalp.

A skull-screw type of electrode, which is used exclusively on animals and never on humans, physically penetrates the bone and is actually screwed through the scalp into the skull. This thick screw electrode too often penetrates the skull to too great a distance causing serious complications. It accordingly also does not define a satisfactory unipolar electrode.

OBJECTS OF THE INVENTION

Accordingly, it is the principal object of the present invention to provide an improved device for monitoring EPs and EEGs.

Another object of the present invention is to provide an improved method for monitoring EPs and EEGs.

A further object of the present invention is to provide a novel and improved unipolar scalp electrode for monitoring the electrical activity of the brain.

A still further object of the present invention is to provide an improved unipolar scalp electrode for monitoring the electrical activity of the brain which maintains improved adhesion to the scalp despite the passage of time and the patient's sweating and/or movement.

Another object is to provide an improved unipolar electrode that maintains its position on the subject so that an unaltered electrical signal can be maintained.

A further object is to provide a novel unipolar electrode which can be readily, precisely and firmly positioned in the scalp but without actually penetrating into the skull or other underlying bone structure.

A still further object is to provide a novel unipolar electrode which is easily sterilized and can be placed in a sterile environment for the monitoring of the electrical activity of the brain, and which further does not require the use of conductive pastes or adhesive tapes.

Another object is to provide a novel unipolar electrode for the monitoring of the electrical activity of the brain which attains consistently low electrical impedances of 2000 ohms or less.

A further object is to provide an improved unipolar electrode for monitoring the electrical activity of the nervous system including the brain and spinal cord which is reliably self-retaining on the patient.

A still further object is to provide a novel disposable unipolar electrode which firmly adheres to the patient's skin.

Another object is to provide a novel disposable unipolar electrode and sterile packaging therefor.

A further object is to provide a novel unipolar electrode which presents a low profile.

Other objects and advantages of the present invention will become more apparent to those persons having ordinary skill in the art to which the present invention pertains from the following description taken in conjunction with the accompanying drawings.

BRIEF DESCRIPTION OF THE DRAWINGS

FIG. 8 is a perspective view of another electrode embodiment of the present invention.

FIG. 9 is a fragmentary side elevational view of another electrode embodiment of the present invention.

FIG. 10 is a side view of another electrode embodiment of the present invention.

FIG. 11 is a bottom view of the electrode of FIG. 10.

FIG. 12 is a perspective view of another electrode embodiment of the present invention.

FIG. 13 is a front end view of the electrode of FIG. 12.

FIG. 14 is a fragmentary side elevational view of another electrode embodiment of the present invention.

FIG. 15 is a side elevational view of another electrode embodiment of the present invention.

FIG. 16 is a side elevational view of another electrode embodiment of the present invention.

FIG. 17 is a side elevational view of another electrode embodiment of the present invention.

FIG. 18 is a side elevational view of the electrode of FIG. 14 illustrating the use of a novel sanitary cover.

FIG. 19 is a side elevational view of the electrode of FIG. 14 showing an alternative wire connector.

FIG. 20 is a side elevational view similar to FIG. 19 illustrating another alternative wire connector.

FIG. 21 is a fragmentary side elevational view of another electrode embodiment of the present invention.

FIG. 25 is a schematic view of a system for monitoring EEGs according to the present invention.

FIG. 26 is a schematic view of a system for monitoring EPs according to the present invention.

DETAILED DESCRIPTION OF THE INVENTION

Figure 1:
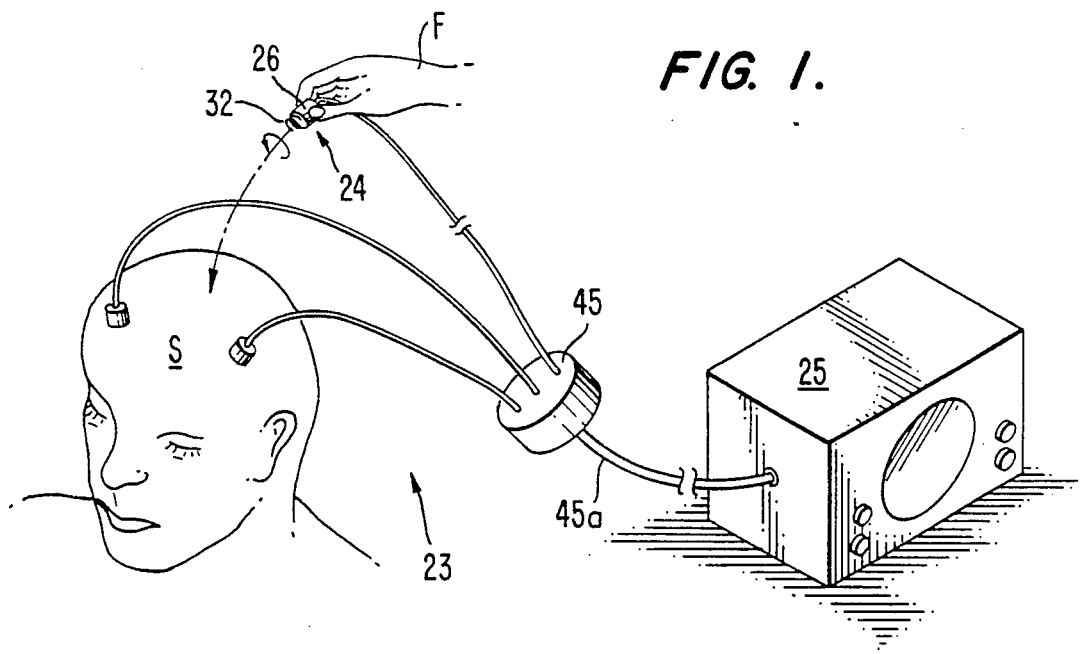
FIG. 1 is a perspective view of a device embodying the present invention shown in its working environment.
Figure 2:
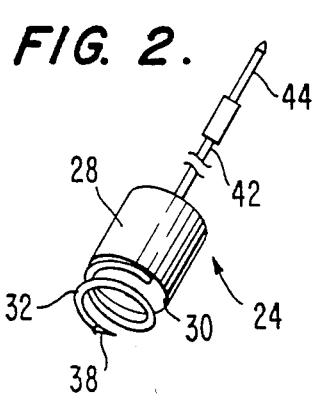
FIG. 2 is a perspective view of the unipolar electrode of FIG. 1 shown in isolation.

Referring to FIG. 1, a system embodying the present invention is illustrated generally at 23. It is shown to comprise a unipolar electrode shown generally at 24 which can be secured to the scalp S and which can be connected at its opposite end to a suitable monitoring device shown in block form at 25 for monitoring the electrical activity of the brain, including EEGs and EPs. Such devices include the "Compact Four" and "Pathfinder" manufactured by Nicolet Biomedical, Inc. of Madison, Wis., the "Lifescan" manufactured by Neuromatics of San Diego, Calif., and the "EPA40A Sensor" manufactured by TECA of Pleasantville, N.Y. Unipolar electrode 24 is shown to comprise a solid cylindrical holder member 26 formed of a nonconductive material such as plastic, and having a generally cylindrical outer surface 28 with a front edge 30. Holder member 26 will typically be 0.5 to 1.0 centimeters in length and have a diameter of 0.5 to 0.6 centimeters. Holder member 26 is adapted to hold the spiral coil 32 embedded therein which is secured at its rearward coil end to holder member 26.

Figure 3:
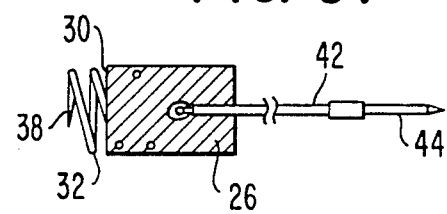
FIG. 3 is a cross sectional side view of the electrode of FIG. 2.
Figure 4:
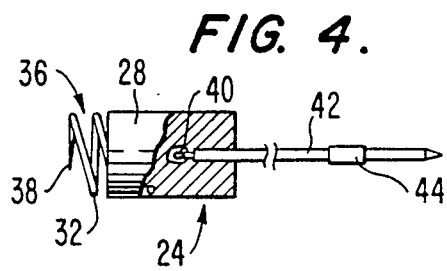
FIG. 4 is a fragmentary side-elevational view of the electrode of FIG. 2.

Spiral coil 32 has its forward portion 36 extending forward of front edge 30 of the holder member. Forward portion 36 will extend forward of front edge 30 approximately 0.15 to 0.3 centimeters. Spiral coil 32 comprises a metal conductive wire, such as silver, platinum, or stainless steel wire of twenty-two or greater gauge, configured to spiral between generally 180 and 720 degrees and ending in a pointed or beveled tip 38. The opposite end 40 of spiral coil 32, best shown in FIGS. 3 and 4, is attached to an electrically conductive wire 42 which transmits the electrical signals from the patient's brain to monitoring device 25. Wire 42 ends in a suitable terminal or pin connector 44 which is adapted to plug into a connector box 45 which in turn is electrically connected via cable 45a to monitoring device 25. Electrically conductive wire 42 rearwardly exits from holder member 26 and is soldered to end 40 providing an electrical connection therebetween.

Unipolar electrode 24 is placed by a physician, or by a trained EEG/EP technician by order of a physician, into the patient's scalp. The physician or technician will firmly grasp holder member surface 28 with the tips of his fingers F and will press tip 38 against the patient's skin, as best shown in FIG. 1. Holder member 26 is then rotated clockwise between 180 and 720 degrees, or until its front edge 30 is flush with the skin, and spiral coil 32 has been rotated securely into the epidermis of the scalp, but not so far that it penetrates the skull or underlying bone itself. After it has been secured to the scalp by reason of its unique spiral configuration, electrically conductive wire 42 is then connected via connector 44 to monitoring device 25.

Electrode 24 which is used in EP and EEG monitoring is unipolar, that is one unit contains one electrode. This means that one electrode is an active electrode picking up a signal while another is a reference, or an inactive, electrode. Depending on what is specifically of interest, the electrode that was used as a reference electrode in one instance can later become an active electrode by electrically switching them. Referring to FIG. 1, typically four to eleven, or as many as twenty-four, unipolar electrodes will be used.

Figure 5:
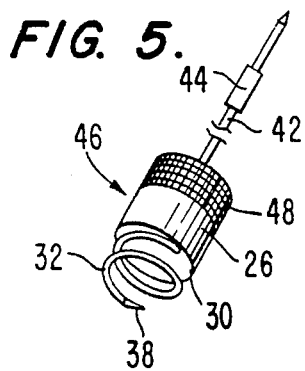
FIG. 5 is a perspective view similar to that of FIG. 2 illustrating another electrode embodiment of the present invention.
Figure 6:
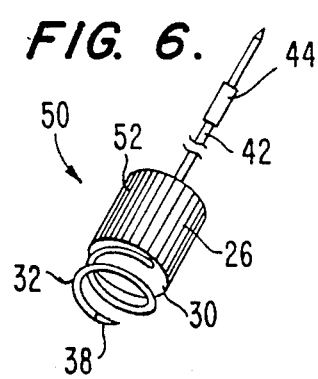
FIG. 6 is a perspective view of another electrode embodiment of the present invention.
Figure 7:
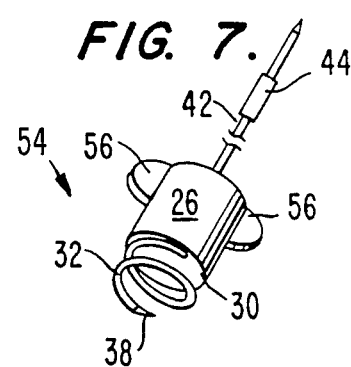
FIG. 7 is a perspective view of another electrode embodiment of the present invention.

To assist in the firm grasping of holder member surface 28, alternative embodiments of the subject unipolar electrode are illustrated. Each of these has a friction increasing means for aiding in the grasping of the holder member to insure that it is quickly, easily and accurately inserted in scalp S. FIG. 5, for example, shows an electrode 46 having a rough, irregular or abraded (cross knurled) exterior rearward surface portion 48 providing this friction increasing means. FIG. 6 shows an electrode 50 wherein holder member 26 has a ribbed or ridged (parallel knurled) surface 52 wherein the ribs extend longitudinally the length of the member. FIG. 7 shows an electrode 54 with its holder member having a pair of opposite protruding ears or wing members 56, which will be grasped by the physician when applying or removing electrode 54, and aid in the rotation thereof.

Further embodiments of the present unipolar electrode design concept are illustrated in FIGS. 8 through 21. FIG. 8 shows an electrode 58 comprising a short screw 60 in which the threads thereof are exaggerated to increase the contact surface area and to better grasp the scalp, but to not penetrate the skull. Flanged surface 62 is provided for ease of grasping and application. The unipolar electrode 64 of FIG. 9 has a straight piercing element 66 comprising the conductive electrode portion and a spiral portion 68 comprising the non-active component designed to retain electrode 64 in the scalp. Unipolar electrode 70 of FIGS. 10 and 11 illustrates a novel design including a spring-loaded clip 72 with sharp teeth 74 in conjunction with an interior straight piercing electrode member 76. Clip 72 forms the retaining portion of the electrode with teeth 74 engaging the skin and holding the electrode thereto. FIGS. 12 and 13 show an electrode 78 comprising a bi-spiral unipolar electrode. As shown it has a pair of electrode wires 80 and 82, each with bevel ends, exiting from the holder member one hundred and eighty degrees from each other, each with a spiral of one hundred and eighty degrees. Each wire 80 and 82 is embedded in the holder member and is soldered at 84 to the electrically conducting wire, as best shown in FIG. 12.

FIG. 14 illustrates another unipolar electrode 86 according to the present invention which is one of the preferred embodiments. Referring thereto it is seen that its holder member 88 is shaped in a flattened spherical configuration thereby providing a low profile from the skin. This is a less obtrusive design which does not protrude so far from the skin when secured thereto as to be likely to be dislodged. Holder member 88 is one cm in diameter and 0.4 cm high. Attached on the top is a pair of opposed ears or wings 90 protruding out from the surface. These wings or ears are similar to wing members 56 of the embodiment of FIG. 7. As can be appreciated, wings 90 provide surfaces for easily grasping holder member 88 and twisting or rotating it in the skin. An electrical wire 92 exits from the top in a manner similar to that of the above-described electrodes. In electrical connection therewith is the spiral coil 94 which is approximately 0.5 cm wide (diameter) and protrudes down from and below the bottom surface 96 of holder member 88. Bottom surface 96 has a concave configuration and the lower tip 98 of spiral coil 94 is slightly below, approximately one-quarter turn, the plane of the forward edge 100 of this surface. Thus, when holder member 88 is grasped and pressed against the subject's skin and twisted, a slight suction will be created thereby better holding electrode 86 to the skin.

FIG. 15 shows a variation on the electrode of FIG. 14. Referring thereto it is seen that electrode 102 instead of a concave bottom surface has a flat bottom surface 104 and the spiral coil 106 then extends down below surface 104. It is also within the scope of this invention to provide in lieu of or in conjunction with the wings or ears a plastic surface which by its very nature is friction producing such as rubber. Alternatively, the outer surface 107 can be abraded as shown by electrode 108 in FIG. 16 and similar to the teachings of the electrode of FIG. 6. In lieu of the wings, a beveled surface 110 defining an upper disc or knob 111 can be provided, as illustrated by electrode 112 in FIG. 17. The outer edge 114 of knob 111 can be easily grasped by the physician's fingers and twisted.

For sanitary purposes it is necessary to sterilize or sanitize at least the coil portion of the electrode. It however is probably not necessary that the entire holder member be sterilized. For sterile packaging purposes each electrode 24 could be packaged in its own individually sealed package. Alternatively, a number of electrodes can be conveniently placed in a single package and only the relevant electrode portions sealed with plastic or other suitable material. This alternative is illustrated in FIG. 18 wherein the plastic cover 117 is illustrated. It covers the bottom surface of the holder member including the coil and is secured to the lower sides of holder member 118 by being slightly smaller in diameter and stretched over the forward edge of the electrode and easily removed by simply grasping one edge.

In the previously disclosed embodiments the outwardly or rearwardly exiting connector wire such as at 42 was permanently secured by soldering or other suitable means to the coil as at 40, as shown in FIGS. 4 and 12, and the opposite end of the connector wire had a connector end such as pin connector 44 which was connected to monitoring device 24. Alternatively, the wires can be permanently connected to the device or connector box 45 and the opposite ends define a removable end. This removable end would then be mated with the corresponding mating portion of the holder member. Thus, it would not be necessary each time to replace the wire, but, rather, only the holder member and attached spiral coil would need to be replaced. One method of doing this is illustrated in FIG. 19. Referring thereto, it is seen that the holder member 122 is provided with a female connector 124 on its upper surface 126 and the wire 128 is provided with a male connector 130 at its end for connecting into female connector 124. Male connector 130 can then be snapped or twisted into or out of female connector 124. The reverse is also possible, as is illustrated in FIG. 20 wherein the wire 132 has a female member 134 at its end and the holder member 136 has a male member 138 on its upper surface 140 and female member 134 is then fitted over male member 138 for attachment and removed for electrode replacement purposes.

Referring to FIG. 21, another unipolar electrode is illustrated generally at 142 and it also is one of the preferred designs illustrated herein. As shown, holder member 144 of electrode 142 is formed by two separable parts—base 146 and cap 148. Cap 148 has a sleeve 150 extending at right angles thereto through which electrode wire 152 passes. Sleeve 150 positions wire 152 so that it does not protrude out of the top of the holder member but out the side or back to present a lower overall electrode profile. Wire 152 at its holder member end has a protruding male end 154 which is received within the opposite female end 156 when cap 148 is fitted to base 146 providing an electrical connection with spiral coil 157. Base 146 on its upper surface has an annular groove into which the lower rim 158 of cap 148 snaps. Once snapped into place cap 148 is free to rotate relative to the monitoring device. Base 146 is secured to the scalp by grasping annular knob 160 and twisting base 146 until spiral coil 157 has penetrated the desired distance into the patient. Cap 148 is snapped into place on base 146 preferably after base 146 has been secured into place on the patient and rotated so that sleeve 150 points towards the monitoring device. It is also within the scope of the present invention to position the annular groove (female portion) on cap 148 and the rim (male member) on base 146, and then snap base 146 into cap 148.

Figure 22:
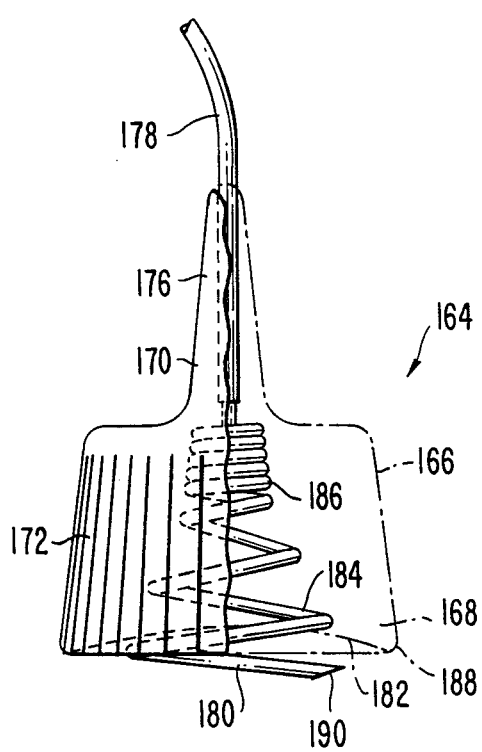
FIG. 22 is a fragmentary side elevational view of another electrode embodiment of the present invention.
Figure 23:
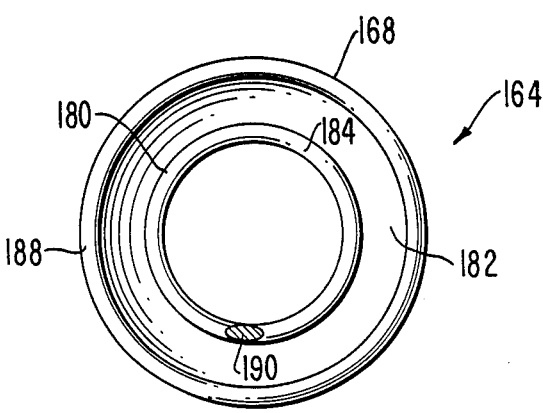
FIG. 23 is a bottom view of the electrode of FIG. 22.

Referring to FIG. 22, another unipolar electrode is illustrated generally at 164 and it is also one of the preferred designs illustrated herein. As shown, the user holder member 166 of electrode 164 has a lower portion 168 and an upper portion 170 connected thereto and formed as one piece therewith. Lower portion 168 has a cylindrical slightly tapering configuration. On its outer surface it has a vertically ribbed configuration 172 similar to that described, for example, in the embodiments of FIGS. 6 and 16. Ribbed configuration 172 increases the grasping or friction surface so that electrode 164 can be easily grasped by the user's fingers and twisted into position. In lieu thereof, any of the previously-described friction increasing means can be used such as the ears or wings of the electrode of FIG. 14. Upper portion 170 further defines an upwardly tapering sleeve 176 through which the exit wire 178 passes. The spiral coil 180 is contained and held within lower portion 168 and extends out of the lower concave surface 182 thereof similar to the electrode embodiment of FIG. 21. Spiral coil 180 extends generally one hundred and eighty to seven hundred and twenty degrees out of lower concave surface 182. Spiral coil 180 has a unique design wherein its lower coils 184 are spaced and are upwardly tapering so as to generally define a cone, and its upper coils 186 are adjacent one another, tightly wound, and define a narrow cylinder Exit wire 178 then is connected to the upper end of upper coils 186, or fits in the central opening thereby defined. The bottom profile of electrode 164 is best illustrated in FIG. 23 and it shows the body-contacting circumferential rim 188 of holder member 166, concave surface 182 and the exposed portion of lower coils 184 of spiral coil 178 which end in a beveled tip 190.

Figure 24:
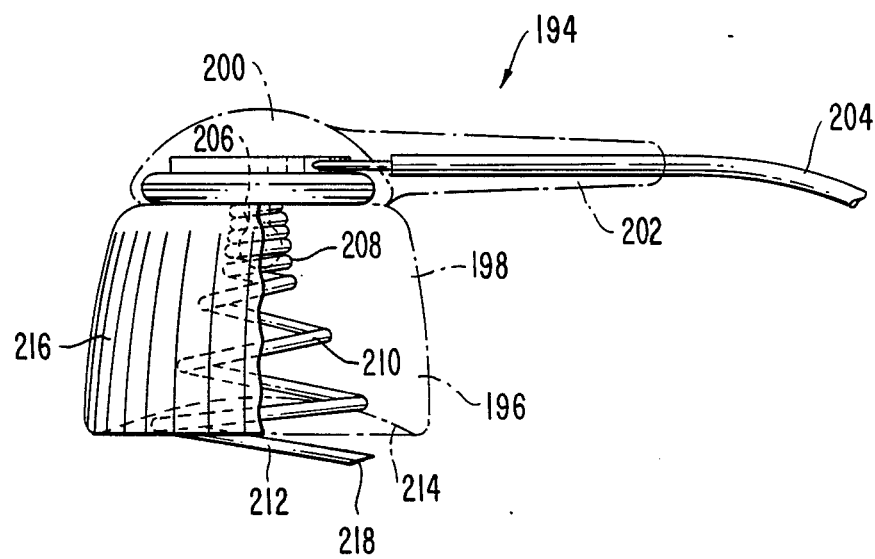
FIG. 24 is a fragmentary side elevational view of another electrode embodiment of the present invention.

Another preferred embodiment of the subject unipolar electrode design is illustrated in FIG. 24, generally at 194. As illustrated, electrode 194 presents a desirably low overall profile. Similar to the embodiment of FIG. 21, it comprises a holder member 196, having two separable parts—base 198 and cap 200. Cap 200 has a generally horizontal sleeve 202 for containing and directing the electrode exit wire 204. Cap 200 then snaps into base 198, or, alternatively, base 198 can snap into a groove of the cap 200, similar to the design as described for FIG. 21. Cap 200 then can rotate relative to base 198 to direct sleeve 202 and thus exit wire 204 towards the monitoring device. Similar to the embodiment of FIG. 21, an electrode male member 206 extends down from cap 200 and is an electrical connection with exit wire 204. Cap 200 then fits into the longitudinal opening defined by the tightly wound coils 208 of the upper portion of spiral coil 210. Similar to the embodiment of FIGS. 22 and 23, the upper tightly wound coils 208 are merely an upper extension of the lower spaced coils 212 of spiral coil 210 and are constructed in one continuous piece, preferably of twenty to twenty-five gauge wire. Lower coils 212 are similarly spaced and tapered to define a cone. Spiral coil 210 extends out through the lower concave surface 214 of base 198 and exits for about 180 to 720 degree turns. This construction is easy to construct and easy to install by simply grasping the outer ribbed portion 216 of base 198, twisting it so that the pointed tip 218 of spiral coil 210 pierces the skin and and spiral coil 210 then enters the skin, generally a single turn. Concave surface 214 will then with pressure applied define a partial vacuum to better hold electrode 194 to the patient. Either before or after twisting spiral coil 210 into the patient, upper cap 200 is snapped into position on base 198, similar to the electrode of FIG. 21. Cap 200 can then be oriented so that sleeve 202 points towards the monitoring device and exit wire 204 is better directed towards the device, preventing tangling of the wires and defining a lower electrode profile.

The present system for monitoring the electrical activity of the brain is illustrated schematically in FIGS. 25 and 26, for monitoring EEGs and EPs, respectively. It essentially comprises a unipolar electrode 24 according to any one of the previously-described designs. The electrode according to its unique spiral coil configuration is firmly secured to the scalp S and accurately and consistently obtains the electrical signal from the brain. An amplifier/preamplifier arrangement shown generally at 224 electrically enhances the signal obtained from the electrode and transmits it to a means for recording, storing and displaying these signals. Typically the amount of amplification for a EEG or EP is several thousand times. For EEGs and EPs a multiple channel input is required. The data generated are permanently recorded via an x,y recorder 226. For EP monitoring a computer 228 is required to average several evoked potentials elicited in response to repeated stimuli 230 to separate the evoked response (signal) from the background EEG (noise). The multiple evoked potentials are summated and averaged in the computer memory while the random background EEG averages out to zero. Because the evoked potential is time-locked to the repetitive stimulus, this computer averaging method considerably enhances the desired evoked potential. The stored data in the memory can then be displayed on the oscilloscope screen and printed via x,y recorder 226 for a permanent record.

It is thus seen that the present unipolar spiral electrode can be efficiently and effectively used to monitor EPs and EEGs in the operating room, in the intensive care unit, and in the clinical neurophysiology laboratory. The unipolar electrode of the subject invention is easily sterilized and consistently results in low electrical impedances. Furthermore, because of its unique spiral coil configuration, the electrode is selfretaining and will remain firmly in place for long periods of time. These features combine to yield highly reproducible recordings of neurophysiological potentials.

From the foregoing detailed description it will be evident that there are a number of changes, adaptations, and modifications of the present invention which come within the province of those skilled in the art. However, it is intended that all such variations not departing from the spirit of the invention be considered as within the scope thereof as limited solely by the appended claims.

We claim:

1. A unipolar electrode for monitoring the electrical activity of the brain of a subject comprising:
a user holder member formed of a non-conductive material and having a forward concave surface and an outside surface adapted to be grasped by the user's fingers,
said user holder member including a friction increasing means on said outside surface which is adapted to be grasped by the user's fingers to aid in the grasping and rotation of said holder member relative to the subject,
a spiral coil formed of a conductive material and having a pointed tip extending out from said forward concave surface and away from said holder member,
said spiral coil spiraling generally between 180 and 720 degrees out from said forward concave surface,
an attaching means for attaching said holder member to said spiral coil such that when said user holder member is grasped on said friction increasing means by the user'fingers, pressed against the subject's skin and rotated, said pointed tip pierces the subject's skin and said spiral coil is twisted into the subject's dermis to a distance sufficient to secure said holder member to the subject but not great enough to pierce the subject's underlying bone,
an electrode wire operatively connectable to said spiral coil, exiting generally rearwardly from said holder member generally away from said forward surface and having an opposite terminus connector end adapted to be connected to a monitoring device for monitoring the electrical activity of the brain of the subject, and
said spiral coil having a rearward end and tightly coiled wires at said rearward end providing electrical connection with said electrode wire.

2. The unipolar electrode of claim 1 including, said friction increasing means including said outside surface having an abraded surface portion.

3. The unipolar electrode of claim 1 including, said friction increasing means including at least one wing member protruding out from said outer surface.

4. The unipolar electrode of claim 3 including, said at least one wing member comprising a pair of opposed spaced wing members.

5. The unipolar electrode of claim 1 including, said friction increasing means including a knob fixed to said outside surface.

6. The unipolar electrode of claim 1 including, said friction increasing means including said outside surface being formed of a malleable plastic.

7. The unipolar electrode of claim 1 including, said friction increasing means including said outer surface having a rough texture.

8. The unipolar electrode of claim 1 including, said spiral coil being formed of a wire having a 22 or lesser gauge.

9. The unipolar electrode of claim 1 including, said holder member including a connector member electrically communicating with said spiral coil,
said electrode wire including a connectable end opposite said opposite terminus connector end, and
said connectable end being adapted to be removably electrically coupled to said connector member.

10. The unipolar electrode of claim 9 including, said connector member defining a female member and said connectable end defining a male member adapted to mate with said female member.

11. The unipolar electrode of claim 12 including, said connectable end defining a female member and said connector member defining a male member adapted to mate with said female member.

12. The unipolar electrode of claim 1 including, said holder member defining a flattened spherical portion.

13. The unipolar electrode of claim 1 including, said forward concave surface including a peripheral forward edge generally defining a plane, and
said spiral coil extending from said forward concave surface towards said plane.

14. The unipolar electrode of claim 13 including, said pointed tip being positioned between said plane and said forward concave surface.

15. The unipolar electrode of claim 14 including, a removable cover extending generally in said plane and against said forward edge for sterile packaging of said spiral coil,
said outside surface having a forward surface portion adjacent to said forward edge, and
said removable cover being stretched over said forward edge and secured against said forward surface portion.

16. The unipolar electrode of claim 13 including said spiral coil passing through said plane, and said pointed tip being positioned beyond said plane.

17. The unipolar electrode of claim 1 including, said pointed tip being beveled.

18. The unipolar electrode of claim 1 including, said opposite terminus connector end being a pin connector.

19. The unipolar electrode of claim 1 including, said opposite terminus connector end being fixed to said device.

20. The unipolar electrode of claim 1 including, said tightly coiled wires exiting as a continuous wire with said electrode wire.

21. The unipolar electrode of claim 1 including, said tightly coiled wires defining an opening, and said electrode wire including a male end member adapted to be received within said opening.

22. The unipolar electrode of claim 21 including, said male end member being rotatable within said opening.

23. The unipolar electrode of claim 22 including, said male end member being rotatable generally 360 degrees within said opening maintaining during this rotation constant electrical contact with said tightly coiled wires.

24. The unipolar electrode of claim 1 including, said attaching means directly attaching said holder member to said spiral coil, and
said electrode wire being directly connected to said spiral coil and to said holder member.

25. The unipolar electrode of claim 1 including, said opposite terminus end being adapted to be connected to a device for monitoring evoked potentials.

26. The unipolar electrode of claim 1 including, said opposite terminus end being adapted to be connected to a device for monitoring electroencephalograms.

27. The unipolar electrode of claim 1 including, said rearward end of said spiral coil being positioned rearward of said forward concave surface and within said user holder member.

28. The unipolar electrode of claim 1 including, said tightly coiled wires being adjacent to one another and forming progressively smaller spirals away from said forward concave surface.

29. The unipolar electrode of claim 1 including, said spiral coil being fixed to said user holder member and relative to said friction increasing means.

30. The system of claim 1 including, said friction increasing means comprising a longitudinal ribbed configuration on said outside surface and around said user holder member.

31. The unipolar of claim 1 including, said tightly coiled wire being positioned entirely within said user holder member.

32. The unipolar electrode of claim 31 including, said spiral coil spiraling inside of said holder member and as it passes forwardly out through said forward concave surface.

33. The unipolar electrode of claim 1 including, said spiral coil spiraling inside of said holder member and as it passes forwardly out through said forward concave surface.

34. The unipolar electrode of claim 1 including, said friction increasing means comprising a knurled configuration disposed radially out and between said tightly coiled wires and said forward concave surface.

35. The unipolar electrode of claim 1 including, said forward concave surface including a peripheral forward edge which is smooth and positioned in a single plane so as to evenly and simultaneously contact the subject's skin about the entire circumference of said edge when pressed thereagainst.

36. A unipolar electrode for monitoring the electrical activity of the brain of a subject comprising:
a user holder member formed of a non-conductive material and having a forward concave surface and an outside surface adapted to be grasped by the user's fingers,
said user holder member including a friction increasing means on said outside surface which is adapted to be grasped by the user's fingers and to aid in the grasping and rotation of said holder member relative to the subject,
a spiral coil formed of a conductive material and having a pointed tip extending out from said forward concave surface and away from said holder member,
said forward concave surface including a peripheral forward edge generally defining a plane,
said spiral coil extending from said forward concave surface towards said plane,
said pointed tip being disposed between said forward concave surface and said plane,
a removable protective cover extending across said forward concave surface, generally in said plane, and secured to and about said holder member at a location generally adjacent to said forward edge,
an attaching means for attaching said holder member to said spiral coil such that when said holder member is grasped on said friction increasing means by the user's fingers, pressed against the subject's skin and rotated, said pointed tip pierces the subject's skin and said spiral coil is twisted into the subject's dermis to a distance sufficient to secure said holder member to the subject but not great enough to pierce the subject's underlying bone, and
an electrode wire operatively connectable to said spiral coil, exiting generally rearwardly from said holder member generally away from said forward surface and having an opposite terminus connector end adapted to be connected to a monitoring device for monitoring the electrical activity of the brain of the subject.

37. The unipolar electrode of claim 36 including: said protective cover being formed of a stretchable plastic material.

38. The unipolar electrode of claim 36 including, said protective cover being fitted into place on said holder member about said forward edge when said spiral coil is in a sterile condition.

39. The unipolar electrode of claim 36 including, said spiral coil being fixed to said user holder member and relative to said friction increasing means.

40. The unipolar electrode of claim 36 including, said friction increasing means including longitudinal ribs about said user holder member.

41. The unipolar electrode of claim 36 including, said spiral coil spiraling within said user holder member and as it passes forwardly out through said forward concave surface.

42. A unipolar electrode for monitoring the electrical activity of the brain of a subject, comprising:
a user holder member formed of a non-conductive material and comprising a base having a forward surface and an outside surface adapted to be grasped by the user's fingers,
said base including a friction increasing means on said outside surface which is adapted to be grasped by the user's fingers and to aid in the grasping and rotation of said holder member relative to the subject,
a spiral coil formed of a conductive material, exiting out from said forward surface and having a pointed tip extending away from said holder member,
an attaching means for attaching said holder member to said spiral coil such that when said holder member is grasped on said friction increasing means by the user's fingers, pressed against the subject's skin and rotated, said pointed tip pierces the subject's skin and said spiral coil is twisted into the subject'S dermis to a distance sufficient to secure said holder member to the subject but not great enough to pierce the subject's underlying bone,
an electrode wire operatively connected to said spiral coil and having an opposite terminus connector end adapted to be connected to a monitoring device for monitoring the electrical activity of the brain of the subject, and
said spiral coil having its rearward portion within said base being tightly coiled and providing electrical connection with said electrode wire.

43. The unipolar electrode of claim 42 including, said spiral coil rearward portion defining a continuous wire with said electrode wire.

44. The unipolar electrode of claim 42 including, said user holder member including a sleeve fixed relative to said base and extending rearwardly from said base away from said forward surface, and said electrode wire exiting through said sleeve.

45. A unipolar electrode for monitoring the electrical activity of the brain of a subject, comprising:

a user holding member formed of a non-conductive material and comprising a base having a forward surface and an outside surface adapted to be grasped by the user's fingers, and a sleeve fixed relative to said base and extending rearwardly from said base away from said forward surface, said base including a friction increasing means on said outside surface which is adapted to be grasped by the user's fingers and to aid in the grasping and rotation of said holder member relative to the subject, a spiral coil formed of a conductive material, exiting out from said forward surface and having a pointed tip extending away from said holder member, an attaching means for attaching said holder member to said spiral coil such that when said user holder member is grasped on said friction increasing means by the user's fingers, pressed against the subject's skin and rotated, said pointed tip pierces the subject's skin and said spiral coil is twisted into the subject's dermis to a distance sufficient to secure said holder member to the subject but not great enough to pierce the subject's underlying bone, an electrode wire operatively connected to said spiral coil, exiting generally rearwardly from said holder member through said sleeve and having an opposite terminus connected end adapted to be connected to a monitoring device for monitoring the electrical activity of the brain of the subject, and said spiral coil having its rearward portion within said base being tightly coiled and providing electrical connection with said electrode wire.

46. The unipolar electrode of claim 45 including, said spiral coil rearward portion defining a continuous wire with said electrode wire.

* * * * *